United States Patent
Mehta et al.

(10) Patent No.: US 10,123,711 B2
(45) Date of Patent: Nov. 13, 2018

(54) HEART RATE AND BLOOD OXYGEN MONITORING SYSTEM

(71) Applicant: Maxim Integrated Products, Inc., San Jose, CA (US)

(72) Inventors: Arpit Mehta, Milpitas, CA (US); Richard I. Olsen, Truckee, CA (US); Daniel S. Christman, Campbell, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 115 days.

(21) Appl. No.: 14/371,174

(22) PCT Filed: Jan. 10, 2013

(86) PCT No.: PCT/US2013/021084
§ 371 (c)(1),
(2) Date: Jul. 10, 2014

(87) PCT Pub. No.: WO2013/106607
PCT Pub. Date: Jul. 18, 2013

(65) Prior Publication Data
US 2015/0011851 A1    Jan. 8, 2015

Related U.S. Application Data

(60) Provisional application No. 61/585,220, filed on Jan. 10, 2012.

(51) Int. Cl.
*A61B 5/1455* (2006.01)
*A61B 5/024* (2006.01)
*A61B 5/00* (2006.01)

(52) U.S. Cl.
CPC ...... *A61B 5/02433* (2013.01); *A61B 5/14552* (2013.01); *A61B 5/6898* (2013.01); *A61B 5/7221* (2013.01); *A61B 5/7257* (2013.01)

(58) Field of Classification Search
CPC ............ A61B 5/14551; A61B 5/02416; A61B 5/14552; A61B 5/7207; A61B 5/4818; A61B 5/0002; A61B 5/0059; A61B 5/0205; A61B 5/024; A61B 5/02427; A61B 5/1455; A61B 5/68; A61B 5/6802; A61B 5/6813; A61B 5/6825; A61B 5/6826
See application file for complete search history.

(56) References Cited

U.S. PATENT DOCUMENTS 4,258,719 A * 3/1981 Lewyn ............... A61B 5/02416
307/650
4,700,708 A * 10/1987 New, Jr. ............. A61B 5/14552
250/252.1

(Continued)

*Primary Examiner* — Eric Winakur
*Assistant Examiner* — Chu Chuan (JJ) Liu
(74) *Attorney, Agent, or Firm* — TIPS Group

(57) ABSTRACT

An integrated circuit device includes an insulating body provided with a number of electrically conductive leads and having a surface provided with a red LED aperture, an IR LED aperture and a photodetector aperture. The insulating body also includes an optical isolator optically separating the photodetector aperture from the red LED aperture and the IR LED aperture. A red LED is aligned with the red LED aperture, an IR LED is aligned with the IR LED aperture, and a photodetector is aligned with the photodetector aperture.

6 Claims, 6 Drawing Sheets

(56) References Cited

U.S. PATENT DOCUMENTS

| | | | | |
|---|---|---|---|---|
| 4,859,057 A * | 8/1989 | Taylor | A61B 5/14552 | 600/323 |
| 4,880,304 A * | 11/1989 | Jaeb | A61B 5/14552 | 356/41 |
| 5,203,329 A * | 4/1993 | Takatani | A61B 5/14552 | 356/41 |
| 5,339,810 A * | 8/1994 | Ivers | A61B 5/02422 | 600/323 |
| 5,469,845 A * | 11/1995 | Delonzor | A61B 5/02427 | 356/41 |
| 5,490,523 A * | 2/1996 | Isaacson | A61B 5/02427 | 600/323 |
| 5,638,818 A * | 6/1997 | Diab | A61B 5/14552 | 356/41 |
| 5,853,364 A * | 12/1998 | Baker, Jr. | A61B 5/02416 | 600/300 |
| 6,198,951 B1 * | 3/2001 | Kosuda | A61B 5/02416 | 600/323 |
| 6,402,690 B1 * | 6/2002 | Rhee | A61B 5/0002 | 600/300 |
| 6,526,300 B1 * | 2/2003 | Kiani | A61B 5/14552 | 600/322 |
| 6,600,940 B1 * | 7/2003 | Fein | A61B 5/14552 | 600/323 |
| 6,654,621 B2 * | 11/2003 | Palatnik | A61B 5/14552 | 600/322 |
| 7,486,977 B2 * | 2/2009 | Sweitzer | A61B 5/14551 | 600/323 |
| 8,761,853 B2 * | 6/2014 | Thaveeprungsriporn | A61B 5/14551 | 600/322 |
| 2003/0163034 A1 * | 8/2003 | Dekker | A61B 5/0205 | 600/372 |
| 2006/0186322 A1 * | 8/2006 | Matsuyama | H01L 27/14621 | 250/226 |
| 2007/0073119 A1 * | 3/2007 | Wobermin | A61B 5/0017 | 600/323 |
| 2007/0098595 A1 * | 5/2007 | Tam | G01N 21/3151 | 422/82.05 |
| 2008/0076991 A1 * | 3/2008 | Ayers | A61B 5/0205 | 600/324 |
| 2008/0076992 A1 * | 3/2008 | Hete | A61B 5/14551 | 600/324 |
| 2010/0234706 A1 * | 9/2010 | Gilland | A61B 5/14552 | 600/344 |
| 2010/0240972 A1 * | 9/2010 | Neal | A61B 5/14552 | 600/324 |
| 2010/0249550 A1 * | 9/2010 | Lovejoy | A61B 5/14552 | 600/323 |
| 2010/0256470 A1 * | 10/2010 | Miller | A61B 5/14551 | 600/324 |
| 2010/0317937 A1 * | 12/2010 | Kuhn | A61B 5/14552 | 600/323 |
| 2010/0331638 A1 * | 12/2010 | Besko | A61B 5/14552 | 600/323 |
| 2011/0071373 A1 * | 3/2011 | Li | A61B 5/0059 | 600/324 |
| 2013/0060104 A1 * | 3/2013 | Schlottau | A61B 5/14558 | 600/310 |

* cited by examiner

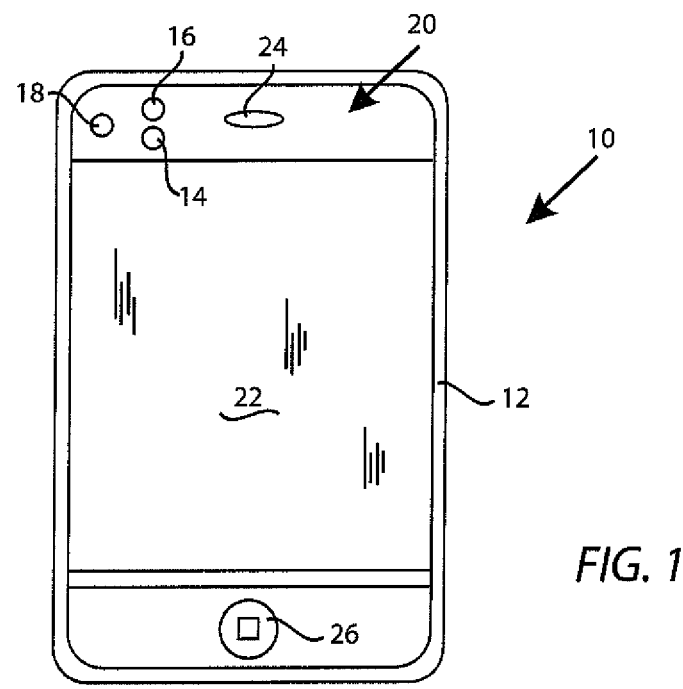
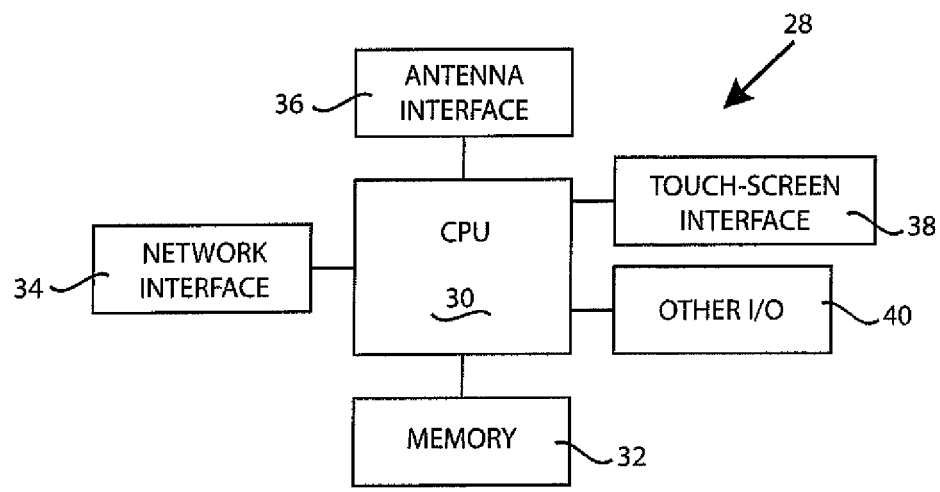
FIG. 1
FIG. 2

HEART RATE AND BLOOD OXYGEN MONITORING SYSTEM

CROSS REFERENCE TO RELATED APPLICATIONS

This application is the US National Stage of International Application No. PCT/US2013/021084, filed Jan. 10, 2013, designating the United States, which claims the benefit of U.S. Ser. No. 61/585,220, filed on Jan. 10, 2012, incorporated by reference.

FIELD OF THE INVENTION

This invention is related to medical devices and more particularly to devices for monitoring heart rate and/or blood oxygen levels.

BACKGROUND OF THE INVENTION

Heart rate monitors and blood oxygen monitors are medical devices used to measure heart rates and blood oxygen levels in real time and/or to record such measurements for later study. Some heart rate monitors use electrodes in contact with a user's skin to measure small electrical signals that are generated by the user's heart as it beats, and other heart rate monitors use light (e.g. IR light) to measure small light fluctuations due to the user's blood circulation. Blood oxygen monitors typically use light (e.g. red light and IR light) to measure the oxygen content of the blood.

Most heart rate monitors which measure light fluctuation are transmissive-type devices which include an infrared (IR) light emitting diode (LED) and a separate photodetector. The IR LED is typically positioned on one side of a finger clip and the photodetector is typically positioned on the other side of the finger clip. In use, the IR light generated by the IR LED is transmitted through the finger, where it is modulated by the blood flow, and is then detected by the photodetector for processing.

Most blood oxygen monitors are also transmissive-type devices which include a red LED, an IR LED and a separate photodetector. The red LED and IR LED are typically positioned on one side of a finger clip and the photodetector is typically positioned on the other side of the finger clip. In use, red light generated by the red LED is transmitted through the finger then is detected by the photodetector for processing.

Medical grade heart rate monitors and blood oxygen monitors have been combined in the past. Even so, they tend to be bulky, cumbersome and expensive. In particular, the medical grade electronics of the monitoring apparatus are typically housed in relatively large chassis and often require filtered wall power to operate. Furthermore, long and cumbersome cables are used couple the monitoring apparatus of the prior art to the finger clips.

Because of the aforementioned problems of traditional medical monitoring equipment, a number of portable, battery powered devices have become available. For example, heart rate monitors including electrodes have been built into a number of devices including wrist watches, exercise equipment, and portable electronic devices such as smartphones. There are also finger clip type transmissive sensors that can be coupled to, for example, a smartphone for detecting heart rate. While less expensive, such devices are also less versatile and tend to have fewer features.

These and other limitations of the prior art will become apparent to those of skill in the art upon a reading of the following descriptions and a study of the several figures of the drawing.

SUMMARY OF THE INVENTION

Various examples are set forth herein for the purpose of illustrating various combinations of elements and acts within the scope of the disclosures of the specification and drawings. As will be apparent to those of skill in the art, other combinations of elements and acts, and variations thereof, are also supported herein.

In an embodiment, set forth by way of example and not limitation, a mobile device with reflectance-based heart rate monitoring includes a body including a transmissive surface, an LED aligned proximate to the transmissive surface, a photodetector aligned with the transmissive surface, monitoring circuitry coupled to the LED and the photodetector to develop a digital output and a CPU coupled to the monitoring circuitry. In an alternate embodiment, the CPU can process the digital signals developed by the monitoring circuitry and at least one of display and store heart rate data.

In a further embodiment, set forth by way of example and not limitation, a heart rate monitoring circuit includes an LED, a photodetector, LED driving circuitry coupled to the LED, a filtering and amplification stage having an input coupled to the photodetector, and an analog-to-digital (A/D) converter having an input coupled to an output of the filtering and amplification stage. In an alternate embodiment, a CPU or other digital processor (such as a digital signal processor, a/k/a "DSP", microprocessor, microcontroller, gate array, state machine, etc.) is coupled to an output of the A/D converter to provide signal processing of heart rate data.

In another embodiment, set forth by way of example and not limitation, a computer implemented process determines if a signal has been acquired and, if so, whether it is strong enough for processing. If no, more power is applied to the LED until the filtered signal is strong enough for processing. Next, if a finger is present long enough to acquire sufficient data for digital processing, digital signal processing takes place to calculate a heart rate. In an alternate embodiment, the heart rate is at least one of display and stored. In a further alternate embodiment, the digital processing includes a Fast Fourier Transform (FFT), windowing, averaging and/or noise rejection. In a still further alternate embodiment, the digital processing includes determining whether a result of the digital processing meets a predetermined confidence level.

In another embodiment, set forth by way of example and not limitation, an electronic device with heart rate monitor includes: a body including at least one infrared (IR) transmissive window; a digital processor located within the body; a display screen supported by the body; an IR light emitting diode (LED) aligned with the IR transmissive window; LED driving circuitry coupled to the IR LED; an IR photodetector aligned with the IR transmissive window; a filtering and amplification stage having an input coupled to the IR photodetector; an analog-to-digital converter (ADC) having an analog input coupled to an output of the filtering and amplification stage and a digital output; and memory coupled to the digital processor. Preferably, the memory includes code segments executable by the digital processor for: (a) detecting that a finger has been placed on the IR transmissive window; (b) capturing raw data from the ADC; (c) performing a Fast Fourier Transform (FFT) of the raw data to develop FFT data; (d) processing the FFT data for at least one of window, averaging and noise rejection; (e) calculating a heart rate; and (f) at least one of displaying and storing the heart rate.

In another embodiment, set forth by way of example and not limitation, an integrated circuit device includes an insulating body provided with a number of electrically conductive leads and having a surface provided with a red LED aperture, an IR LED aperture and a photodetector aperture, the insulating body including an optical isolator separating the photodetector aperture from the red LED aperture and the IR LED aperture. A red LED is aligned with the red LED aperture, an IR LED is aligned with the IR LED aperture, and a photodetector is aligned with the photodetector aperture.

In another embodiment, set forth by way of example and not limitation, a combination heart rate monitor and blood oxygen monitoring circuit includes: a red LED and an IR LED; a red photodetector and an IR photodetector; a filtering and amplification stage coupled to the red photodetector and the IR photodetector; control circuitry receiving feedback from the filtering and amplification stage and controlling the currents to the red LED and the IR LED; and an analog-to-digital converter (ADC) having an analog input coupled to an output of the filtering and amplification stage and having a digital output.

These and other examples of combinations of elements and acts supported herein as well as advantages thereof will become apparent to those of skill in the art upon a reading of the following descriptions and a study of the several figures of the drawing.

BRIEF DESCRIPTION OF THE DRAWINGS

Several examples will now be described with reference to the drawings, wherein like elements and/or acts are provided with like reference numerals. The examples are intended to illustrate, not limit, concepts disclosed herein. The drawings include the following figures:

FIG. 1 is a top plan view of an example reflectance-based heart rate monitoring system built into a smart telephone device;

FIG. 2 is a block diagram of example CPU and related circuitry of the example smart telephone device of FIG. 1;

DETAILED DESCRIPTION OF THE INVENTION

Figure 3:
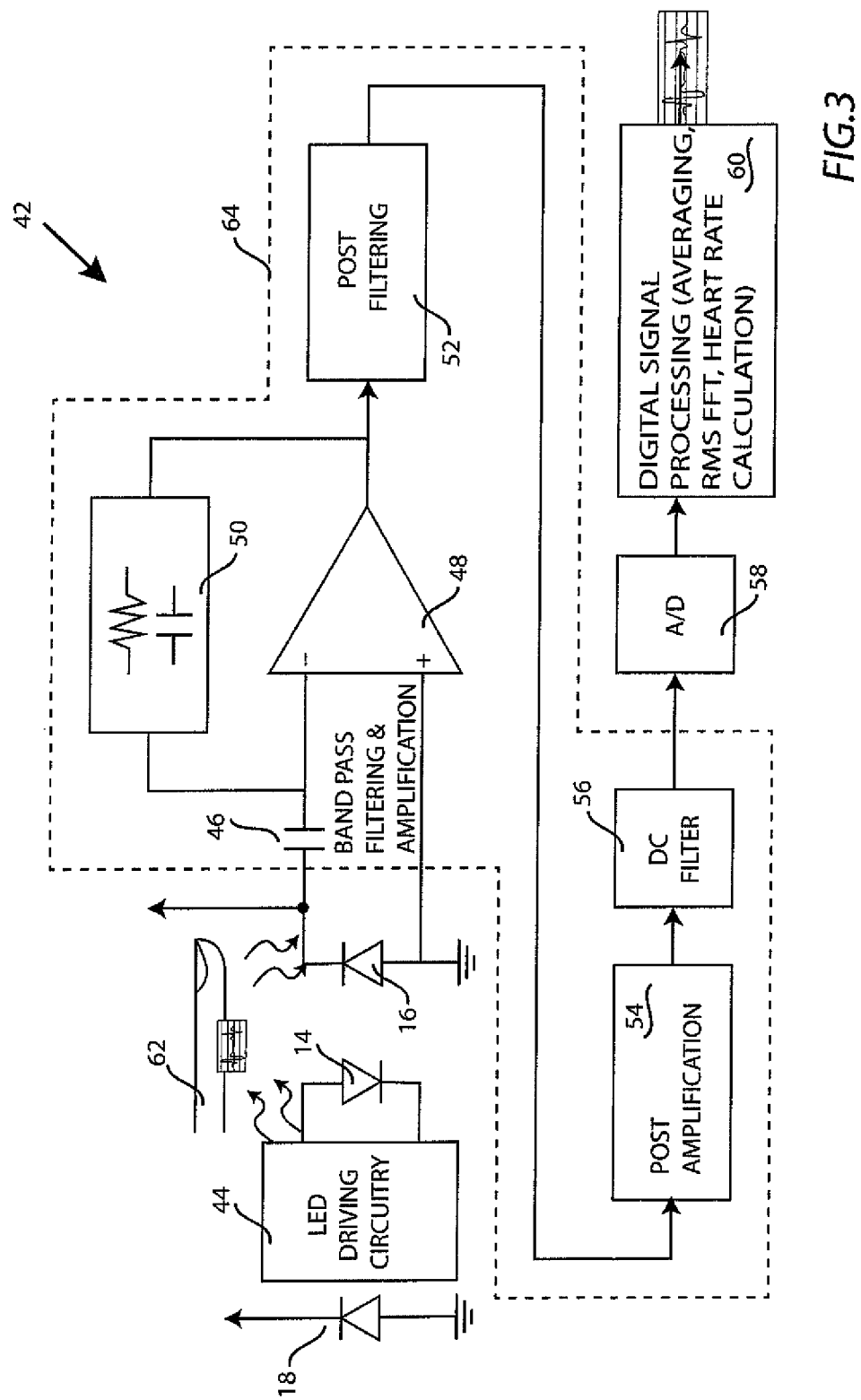
FIG. 3 is a block diagram of example heart rate monitoring circuitry.

FIG. 1 illustrates, by way of example and not limitation, a reflectance-based heart rate monitoring system built into a smartphone 10. In this example, the smartphone 10 includes a body 12, an LED 14, a photodetector 16, a light sensor 18, and a transmissive surface 20 (e.g. a glass or plastic surface). The smartphone 10 further includes a touch-screen 22, a speaker aperture 24, and a control button 26.

The light emitting diode (LED) 14 is a preferred example of a light emitting source, although other light emitting sources may also be suitable in some applications. In an example embodiment, the LED 14 is an infrared (IR) LED such that the light that it emits is generally not detectible by the human eye. The photodetector 16 can be, for example, a photodiode, although other photodetectors may also be suitable for some applications.

In an embodiment, set forth by way of example and not limitation, LED 14 and photodetector 16 are aligned proximate to the transmissive surface 20 (which may be substantially planar) which can serve as a window for the LED 14 and photodetector 16. In this way, if a finger is placed on the transmissive surface 20 over the LED 14 and the photodetector 16, IR light from the LED 14 may reflect off of the finger to the photodetector 16 for the monitoring of heart rate.

FIG. 2 is a block diagram, set forth by way of example and not limitation, of circuitry 28 within the body 12 of smartphone 10. The circuitry includes a CPU 30, memory 32, a network interface 34, an antenna interface 36, a touch-screen interface 38 and other input/output (I/O) circuitry 40. The CPU can be provided by several manufacturing sources, as will be appreciated by those of skill in the art, and the memory 32 can include both volatile and non-volatile memory, both of which are capable of storing data and program code in a non-transitory fashion (e.g. not as a propagating electromagnetic waves). Other forms of non-transitory storage can also be used, as will be appreciated by those of ordinary skill in the art.

FIG. 3 is a block diagram of a heart rate monitoring circuit 42, set forth by way of example and not limitation, which can form a part of the circuitry of FIG. 2. The example circuit 42 includes the light sensor 18, LED driving circuitry 44, the LED 14, photodetector 16, a capacitor 46, an amplifier 48, a resistive-capacitive (R/C) feedback circuit 50, post filtering 52, post amplification 54, a direct current (D.C.) filter 56, an analog-to-digital (A/D) converter 58, and a digital processor 30 (which may be the CPU 30). A finger 62 can be placed in proximity to LED 14 and photodetector 16 to provide data for heart rate calculation in the digital processor 60.

Various portions of the heart rate monitoring circuit 42 may be provided as part or all of an integrated circuit (I.C.). For example, the filtering and amplification stage 64 between the output of the photodetector 16 and the input to the A/D converter 58 can be provided as part or all of an I.C. Furthermore, other components shown in FIG. 3 can be integrated with the filtering and amplification stage 64. Integration is considered to be desirable in compact systems and devices, such as the aforementioned smartphone devices and other devices such as computer tablets, MP3 players, laptop computers, etc.

Figure 4:
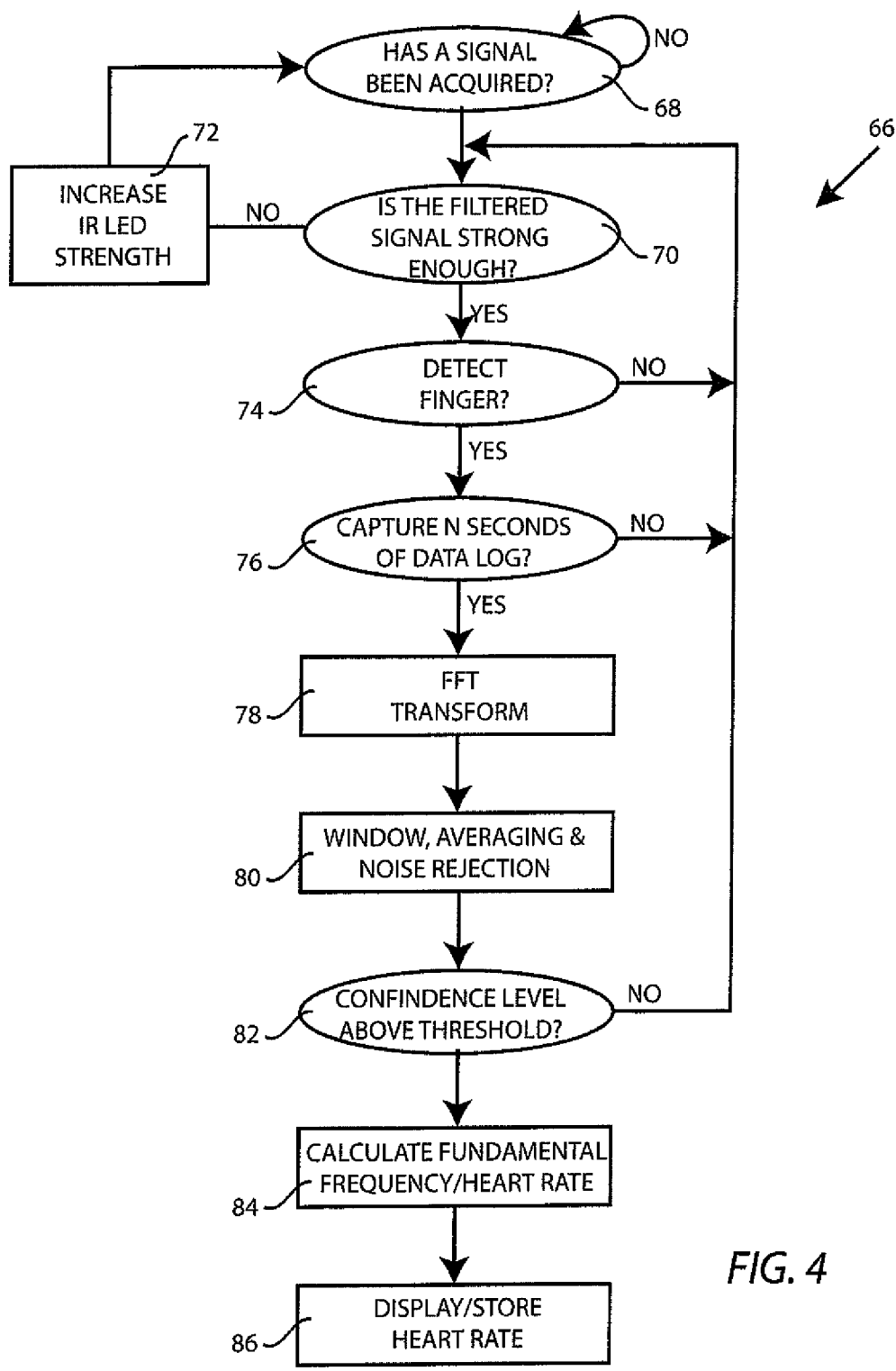
FIG. 4 is a flow diagram of an example process for heart rate monitoring.

FIG. 4 is a flow diagram, set forth by way of example and not limitation, of a process 66 for heart rate monitoring. In this example embodiment, an operation 68 determines if a signal has been acquired, e.g. from photodetector 16. If so, an operation 70 determines if the signal, after filtering, is strong enough for processing. If not, an operation 72 increased the LED strength, e.g. by adjusting the LED driving circuitry 44.

If the filtered signal is strong enough, an operation 74 determines if a finger is detected. If so, an operation captures N seconds of data (e.g. 5 seconds of data) and, in this example, stores the captured data in a data log. Next, after a successful capture of N second of data, a fast Fourier transform (FFT) occurs in an operation 78, and windowing, averaging and noise rejection occurs in an operation 80.

Next, in an operation 82, it is determined whether the confidence level for the data is above a given threshold. For example, the threshold might be, by way of non-limiting examples a 95% or 99% confidence level that there is accurate heart rate data to be processed. If so, the fundamental frequency/heart rate is calculated in an operation 84. An operation 86 can the store the data for later analysis, such as in memory 32, or display the heart rate data, such as on touch-screen 22.

Figure 5:
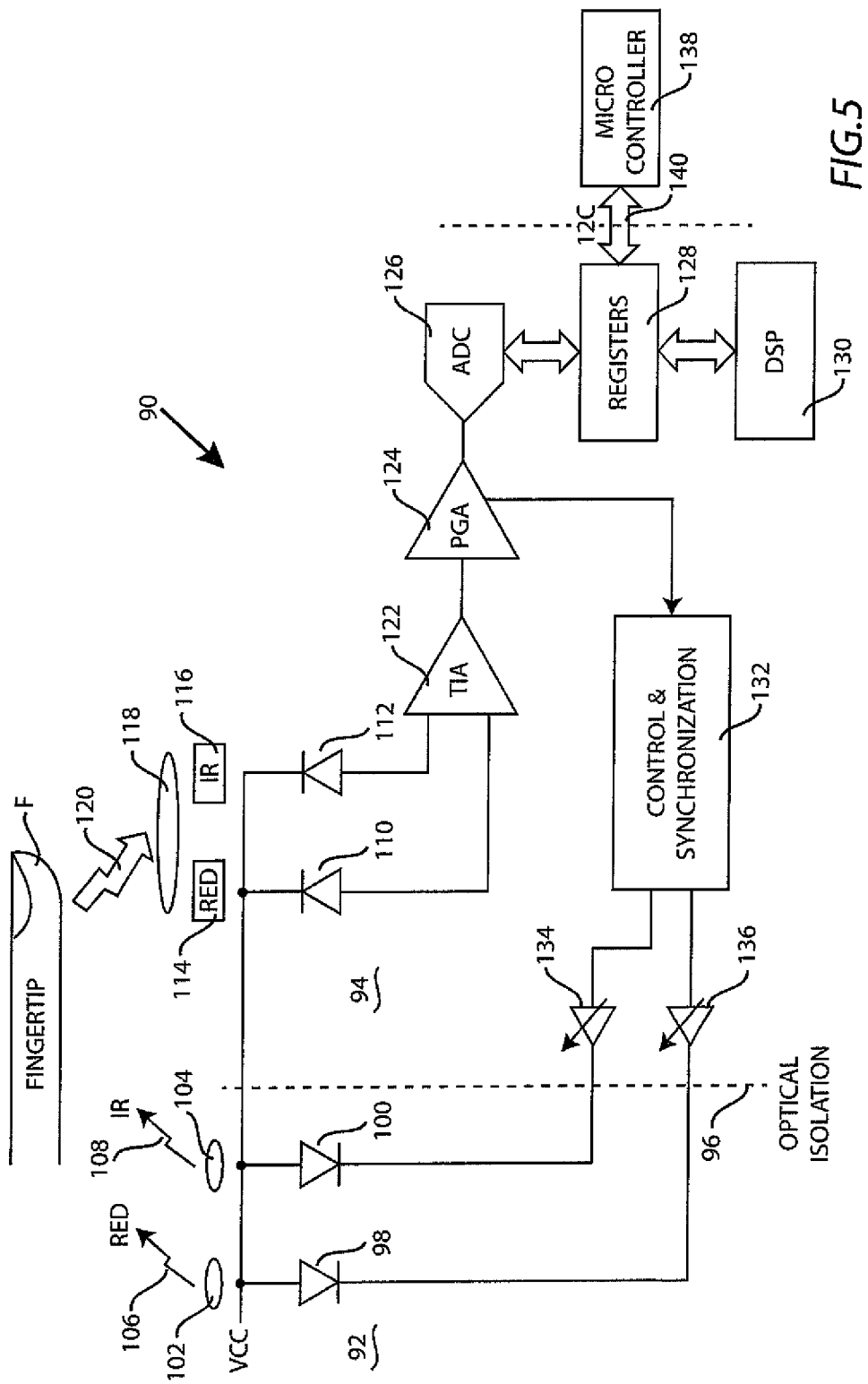
FIG. 5 is a block diagram of an example of a combination heart rate monitor and blood oxygen monitoring circuitry.

FIG. 5 is a block diagram of an example combination heart rate and blood oxygen monitoring system 90 including a light generating section 92 and a light receiving section 94. Preferably, the light generating section 92 and the light receiving section 94 are optically isolated as indicated by the broken line 96. By "light", it is meant herein electromagnetic radiation, visible or not. For example, the light can be in the red or infrared (IR) frequency ranges.

The light generating section 92, in this non-limiting example, includes a red LED 98 and an IR LED 100. Optionally, a lens 102 is aligned with red LED 98 and a lens 104 is aligned with IR LED 100. The anodes of LEDs 98 and 100 are coupled to Vcc, e.g. about 3-5 volts in certain embodiments. When energized, LED 98 develops red light 106 and LED 100 develops IR light 108.

In certain example embodiments LEDs 98 and 100 are pulsed ON and OFF in regular intervals in a time multiplexed manner. In a non-limiting example, the red LED wavelength is centered at about 620 nm and the IR LED wavelength is centered at about 850 nm. Other wavelength centers are available, as will be appreciated by those of skilled in the art.

The light receiving section 94, in this non-limiting example, includes a first photodiode 110 and a second photodiode 112. The photodiodes 110 and 112 may be virtual photodiodes comprising a plurality of photodiodes coupled together or may be a single photodiode functionally separated into the first photodiode and the second photodiode. The cathodes of first photodiode 110 and second photodiode 112 are coupled to Vcc (e.g. they are reversed biased), and are preferably aligned with a first optical filter 114 and a second optical filter 116. In this non-limiting example, first filter 114 is a red filter and second filter 116 is an IR filter. Optionally, a lens 118 is provided to collect reflected light signals 120.

The filters 114 and 116 can be provided by coating photodiodes 110 and 112, respectively, with organic filter pigments which shapes the spectral response of the photodiodes. The use of filters, such as filters 114 and 116, helps to improve "out of band" light rejection and increase overall signal to noise ratio (SNR).

The light receiving section 92, in this non-limiting example, also includes a transimpedance amplifier (TIA) 122, a programmable gain amplifier (PGA) 124, an analog-to-digital converter (ADC) 126, registers 128, a digital signal processor (DSP) 130, control & synchronization 132, drive buffer 134 and drive buffer 136. An optional microcontroller 138 can communicate with registers 128 via a bus 140 by using, by way of non-limiting example, an I2C protocol.

The red LED 98 and IR LED 100 develop red light 106 and IR light 108, respectively, which are directed to a fingertip F. In this example, LEDs 98 and 10 are pulsed ON and OFF at regular intervals in a time multiplexed manner. The timing and current levels for LEDs 98 and 100 are determined by control & synchronization 132 and are provided by drive buffers 136 and 134, respectively.

The red photodiode 110 and IR photodiode 112 receive reflected light signals 120 from fingertip F and convert these light signals into current. The outputs of photodiodes 110 and 112 are applied to TIA 122 for amplification and processing. In this example, TIA 122 converts the photodiode currents into suitable output voltages. Since the signals reflected from the skin can be very small (few mV to uV) and may be associated with common mode voltage levels in the order of several volts, in addition to amplification of the current signal from the photodiodes, TIA also preferably removes unwanted common mode signals and filters for the signals reflected from fingertip F (often around 1.2 Hz). First order filtering can be configured at the TIA stage to extract the AC signals reflected from the skin.

In this non-limiting example, PGA 124 receives signals from TIA 122 and compares them against fixed threshold parameters and adjusts its gain of amplifier appropriately. The PGA 124 also generates feedback signals for control & synchronization 132 which, in turn, controls the drive levels of drive buffers 134 and 136, thereby adjusting the LED signal strength until a target signal amplitude is achieved.

ADC 126 receives analog signals from PGA 124 and converts them to digital signals that can be stored in digital registers 128. The DSP 130, in this non-limiting example, does the post processing of the data stored in the registers 128. For example, DPS 130 can digitally filter the data to remove out-of-band noise, perform averaging, generate Fast Fourier Transform (FFT) signals to calculate heart rate, generate confidence levels of signals, calculate percent oxygen content, store data in look-up tables, etc.

Control & synchronization 132, in this non-limiting example, includes logic circuitry which uses the control signals from PGA 124 to generate control signals for drive buffers 134 and 136 to adjust the intensity of the light generated by the LEDs. Control & synchronization 132 also controls the timing of the firing of the LEDs so they are each illuminated in an appropriate timing interval.

Bus 140, in this non-limiting example, can be used to communicate with external devices (such as microcontroller 138) using an inter-integrated circuit (I2C) interface. In alternate embodiments, microcontroller 138 may be omitted or may be integrated with the circuit 90. As well known to those of skill in the art, an I2C interface is a multi-master serial single-ended computer bus used to connect electronic devices. Other interfaces are also suitable, as will be appreciated by those of skill in the art. In this non-limiting example, microcontroller 138 can access the registers 128 to derive data from the circuit 90. For example, microcontroller 138 can comprise a sensor hub of a smartphone.

Figure 6:
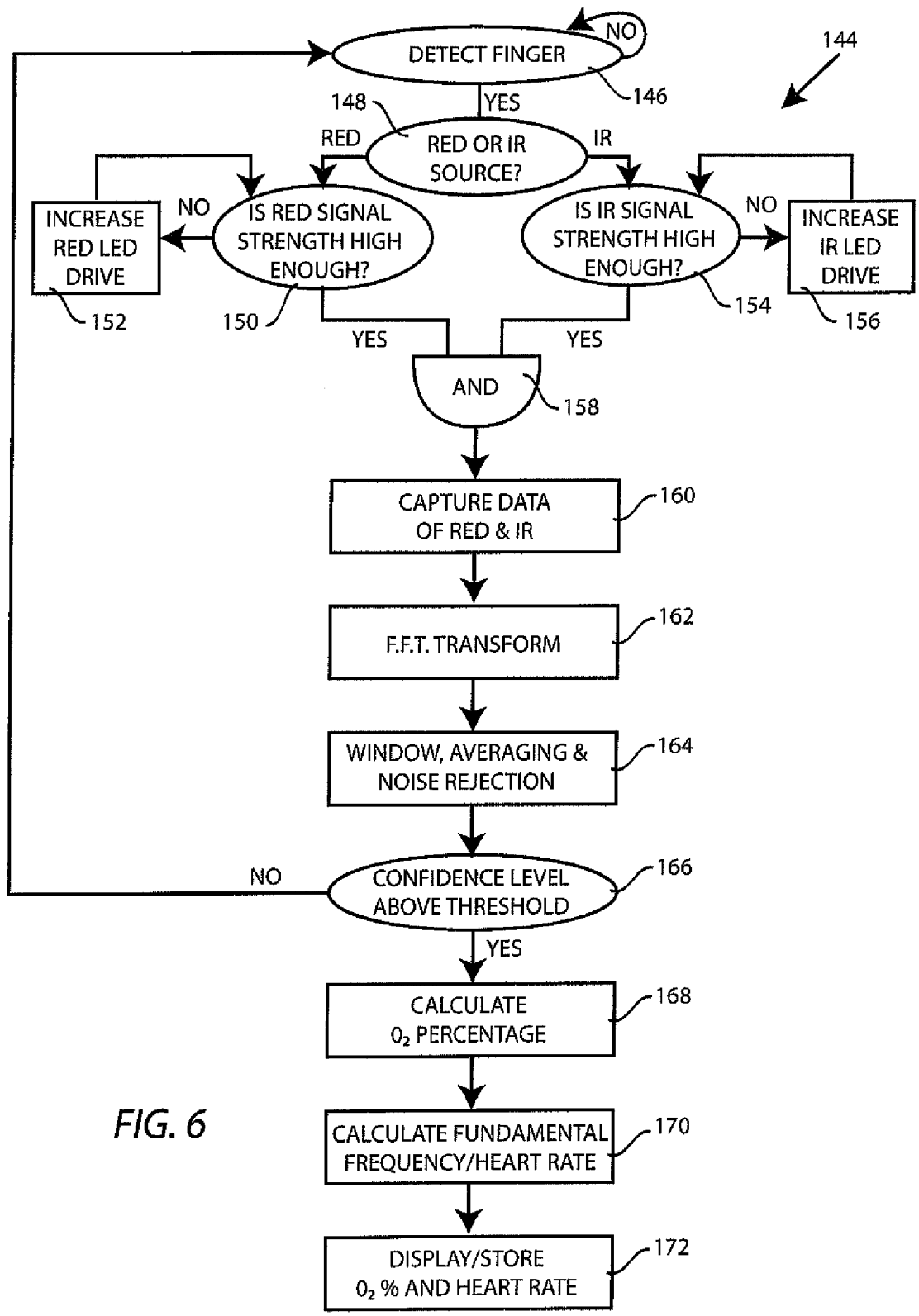
FIG. 6 is a flow diagram of an example process for both heart rate monitoring and blood oxygen level monitoring.

FIG. 6 is a flow diagram of a process 144, set forth by way of example and not limitation, for monitoring heart rate and blood oxygenation. Process 144 idles in an operation 146 until a finger (such as fingertip F of FIG. 5) is detected. If it is detected, it is determined if the red LED 98 or IR LED 100 is the light source. If it is the red LED 98, an operation 150 determines if the red signal strength as detected by photodiode 110 is high enough. If not, the drive current to the red LED 98 is increased via drive buffer 136, in this non-limiting example. Likewise, if the IR LED 100 is providing the illumination, an operation 154 determines if the IR signal strength is high enough. If not, an operation 156 increases the IR LED drive, e.g. by increasing the drive current to IR LED 100 via drive buffer 134.

When both the red and IR signal strength are high enough, as determined by the AND operation 158, an operation 160 captures both red and IR data. This data is processed, for example, with a Fast Fourier Transfer (FFT) in an operation 162 and is further processed in an operation 164 to provide, by way of non-limiting examples, windowing, averaging and/or noise rejection.

Next, in an operation 166, it is determined whether the confidence level in the derived data is above a threshold level. If not, process control is returned to operation 146. If the confidence level is sufficient, the oxygen level in the bloodstream ($O_2$ level) is calculated in an operation 168, and the heart rate (or "fundamental frequency") is calculated in an operation 170. Next, in an operation 172, the heart rate and blood oxygen level is displayed and/or stored in, for example, registers 128.

Figure 7:
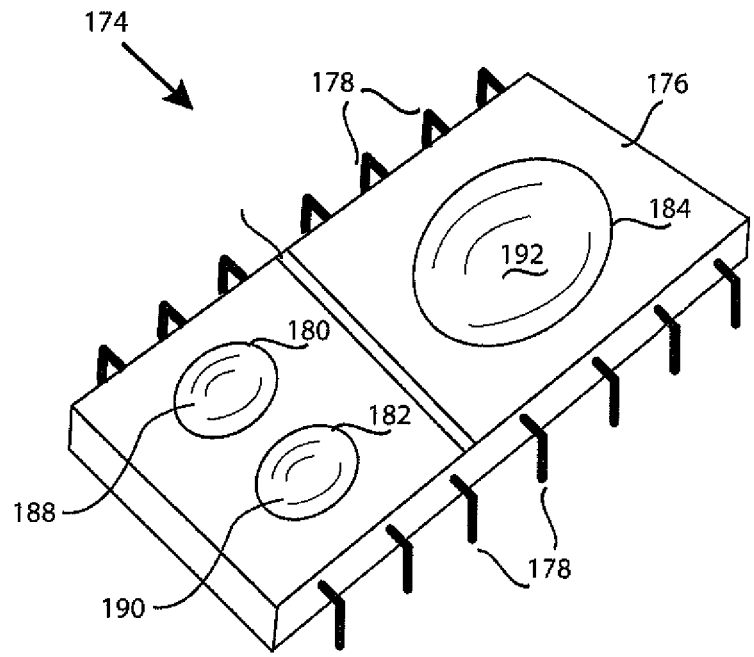
FIG. 7 is a perspective view of an integrated heart rate and blood oxygen sensor.

FIG. 7 is a perspective view of an integrated heart rate and blood oxygen sensor IC 174, set forth by way of example but not limitation. In this example, the sensor IC 174 is illustrated as having an elongated rectangular body 176 provided with a plurality of pins or leads 178. This configuration is sometimes referred to as a dual in-line pin (DIP) package. In this example, there are fourteen electrically conductive (usually metal) leads 178, e.g. seven on each side of the body 176. The body 176 is typically made from a non-conducting material such as plastic or ceramic.

In this example, the body 176 is provided with three apertures 180, 182 and 184 and an optical isolator 186. Also in this example, lenses 188, 190 and 192 are disposed within the apertures 180, 182 and 184, respectively. The lenses are typically made from a plastic material, although lenses of other materials such as glass or quartz are also possible. The optical isolator 186 should be substantially impermeable to light in the red and IR ranges in this example.

With reference to both FIGS. 5 and 7, lenses 188 and 190 of FIG. 7 can, for example, correspond with lenses 102 and 104 of FIG. 5. Lens 192 of FIG. 7 can, by way of non-limiting example, correspond with lens 118 of FIG. 5. The optical isolator 186 of FIG. 7 can, also by way of non-limiting example, correspond with the optical isolation 96 of FIG. 5. The I2C bus of FIG. 5 can correspond, for example, to several of pins 178 of FIG. 7, and Vcc can also be associated with a pin 178 of FIG. 7.

It will therefore be appreciated that the circuitry 90 of FIG. 5 can be incorporated into the body 176 of FIG. 7 with, for example, the light generating section 92 on one side of the optical isolator 186 and the light receiving section 94 on the other side of the optical isolator 186. Other configurations, with more or less components and different positions with respect to the optical isolator are also available, as will be appreciated by those of skill in the art.

Figure 8:
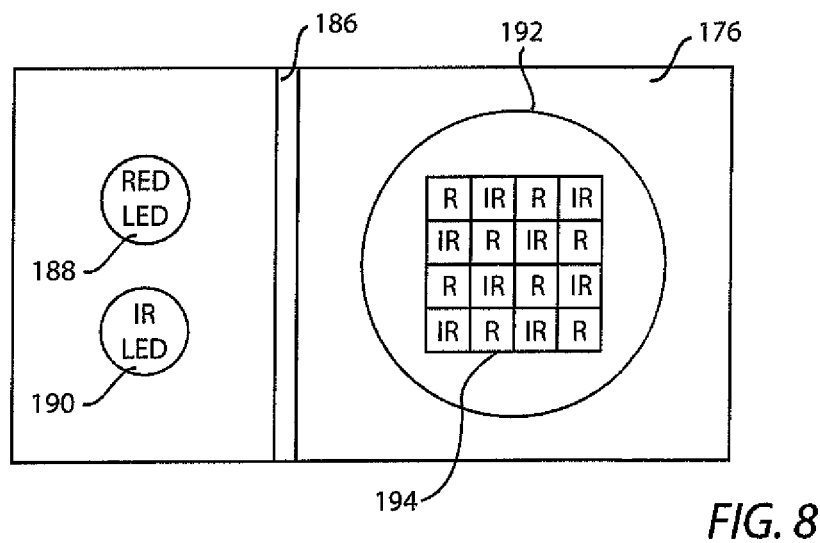
FIG. 8 is a top plan view of the sensor of FIG. 8.

FIG. 8 is a top plan view of the IC 174 of FIG. 7. In this example, the LED beneath the lens 188 is a red LED, and the LED beneath the lens 190 is an IR LED. Beneath the lens 192 is an optical filter array 194 corresponding, in an example embodiment, to filters 114 and 116 of FIG. 5. Here, the optical filter array is formed over the photodetectors as films of organic materials in a grid-like pattern of alternating red (R) and IR filters. By filtering out other wavelengths (e.g. blue or green), the SNR for the detector is improved.

Although various examples have been described using specific terms and devices, such description is for illustrative purposes only. The words used are words of description rather than of limitation. It is to be understood that changes and variations may be made by those of ordinary skill in the art without departing from the spirit or the scope of any examples described herein. In addition, it should be understood that aspects of various other examples may be interchanged either in whole or in part. It is therefore intended that the claims herein and hereafter presented be interpreted in accordance with their true spirit and scope and without limitation or estoppel.

What is claimed is:

1. An electronic device with heart rate monitor comprising:
 a body including a planar infrared (IR) transmissive surface comprising a plastic or glass;
 a digital processor located within the body;
 a display screen supported by the body;
 an IR light emitting diode (LED) aligned with the IR transmissive surface;
 LED driving circuitry coupled to the IR LED;
 an IR photodetector aligned with the IR transmissive surface, where the IR transmissive surface serves as a window for the IR LED and the IR photodetector such that a finger placed on the IR transmissive surface over the IR LED and the IR photodetector will reflect IR light from the IR LED back to the IR photodetector through the window;
 a filtering and amplification stage having an input coupled to the IR photodetector;
 an analog-to-digital converter (ADC) having an analog input coupled to an output of the filtering and amplification stage and a digital output; and
 memory coupled to the digital processor including code segments executable by the digital processor for:
 (a) continuously determining if a signal has been acquired from the IR detector until a signal has been acquired;
 (b) filtering the acquired signal, determining if it is strong enough for processing and, if not, increasing the IR LED strength and returning to operation (a);
 (c) detecting if a finger has been placed on the IR transmissive surface and, if not, returning to operation (b);
 (d) capturing raw data from the ADC and storing the raw data in a data log;
 (e) checking the data log and, if N seconds of raw data has not been captured, returning to operation (b);
 (f) performing a Fast Fourier Transform (FFT) of the raw data to develop FFT data;
 (g) processing the FFT data for at least one of window, averaging and noise rejection to develop processed FFT data;
 (h) determining a confidence level in the processed FFT data and, if the confidence level is not above a threshold, returning to operation (b);
 (i) calculating a heart rate from the processed FFT data; and
 (j) at least one of displaying and storing the heart rate.

2. An electronic device with heart rate monitor as recited in claim 1 wherein the electronic device is a portable digital device and further comprises a wireless connection to a network.

3. An electronic device with heart rate monitor as recited in claim 2 wherein the network is at least one of a cellular telephone network and the Internet.

4. An electronic device with heart rate monitor as recited in claim 3 wherein the electronic device is one of a cellular telephone and a computer tablet.

5. A combination heart rate monitor and blood oxygen monitoring circuit comprising:
 a red LED and an IR LED;
 a time multiplexer pulsing the red LED and the IR LED on and off in regular intervals;
 a red photodetector and an IR photodetector positioned to receive light emitted by the red LED and the IR LED that is reflected from a finger positioned proximate to the red LED, the IR LED, the red photodetector and the IR photodetector;

a filtering and amplification stage coupled to the red photodetector and the IR photodetector to process signals developed from the light reflected by the finger;

control circuitry receiving feedback from the filtering and amplification stage and controlling the currents to the red LED and the IR LED to control the intensity of the light that they emit;

an analog-to-digital converter (ADC) having an analog input coupled to an output of the filtering and amplification stage and having a digital output;

registers for storing digital output of the ADC;

a digital signal processor (DSP) coupled to the registers for processing data stored therein; and memory coupled to the DSP including code segments executable by the DSP for:

(a) continuously determining if a finger has been detected until a finger is detected;
(b) determining if a red LED source or an IR LED source is detected;
(c) if a red LED source has been detected, determining if its signal strength is high enough and, if not, increasing a red LED drive current;
(d) if an IR LED source has been detected, determining if its signal strength is high enough and, if not, increasing an IR LED drive current;
(e) capturing red data and IR data when both the red signal strength and the IR signal strength are high enough;
(f) performing a Fast Fourier Transform (FFT) of the captured red data and captured IR data to develop FFT data;
(g) processing the FFT data for at least one of window, averaging, and noise rejection to develop processed FFT data;
(h) determining a confidence level in the processed FFT data and, if the confidence level is not above a threshold, returning to operation (a);
(i) calculating the blood oxygen level from the processed FFT data;
(j) calculating the heart rate as the fundamental frequency from the processed FFT data; and
(k) at least one of displaying and storing the heart rate and the blood oxygen level.

6. A combination heart rate and blood oxygen monitoring circuit as recited in claim 5 wherein the filtering and amplification stage includes a series connection of a transimpedance amplifier (TIA) and a programmable gain amplifier (PGA).

* * * * *